US008147517B2

(12) United States Patent
Trieu et al.

(10) Patent No.: US 8,147,517 B2
(45) Date of Patent: Apr. 3, 2012

(54) SYSTEMS AND METHODS FOR ADJUSTING PROPERTIES OF A SPINAL IMPLANT

(75) Inventors: Hai H. Trieu, Cordova, TN (US); Eric Christian Lange, Collierville, TN (US); Kent Michael Anderson, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1181 days.

(21) Appl. No.: 11/439,006

(22) Filed: May 23, 2006

(65) Prior Publication Data
US 2007/0276368 A1 Nov. 29, 2007

(51) Int. Cl.
*A61F 2/30* (2006.01)
(52) U.S. Cl. .......................... 606/248; 606/246
(58) Field of Classification Search .... 623/17.11–17.16; 600/594; 606/102, 61, 248–278, 53, 60, 606/246
See application file for complete search history.

(56) References Cited

U.S. PATENT DOCUMENTS

| | | |
|---|---|---|
| 2,077,804 A | 4/1937 | Morrison |
| 2,677,369 A | 5/1954 | Knowles |
| 3,223,083 A | 12/1965 | Cobey ............... 128/92 |
| 3,648,691 A | 3/1972 | Lumb et al. |
| 3,867,728 A | 2/1975 | Stubstad et al. |
| 4,011,602 A | 3/1977 | Rybicki et al. |
| 4,257,409 A | 3/1981 | Bacal et al. |
| 4,289,123 A | 9/1981 | Dunn |
| 4,401,112 A | 8/1983 | Rezaian |
| 4,553,273 A | 11/1985 | Wu |
| 4,554,914 A | 11/1985 | Kapp et al. |
| 4,573,454 A | 3/1986 | Hoffman |
| 4,599,086 A | 7/1986 | Doty |
| 4,604,995 A | 8/1986 | Stephens et al. |
| 4,611,582 A | 9/1986 | Duff |
| 4,632,101 A | 12/1986 | Freedland |
| 4,657,550 A | 4/1987 | Daher |
| 4,686,970 A | 8/1987 | Dove |
| 4,827,918 A | 5/1989 | Olerud |

(Continued)

FOREIGN PATENT DOCUMENTS

DE 2821678 A1 11/1979

(Continued)

OTHER PUBLICATIONS

"Dispositivo Intervertebrale Ammortizzante DIAM," date unknown, p. 1.

(Continued)

*Primary Examiner* — Eduardo C Robert
*Assistant Examiner* — James Palmer

(57) ABSTRACT

A method for controlling properties of a medical implant includes locating the medical implant in an interspinous area between two spinal processes of a person. The medical implant is coupled to a container via a conduit. A fluid is received in an interior of the container in fluid communication with the conduit. The fluid flows from the container toward the implant having an interior configured to receive the fluid. A pressure sensor is coupled to the interior of the container and/or an interior of the conduit. An internal pressure is determined of the interior of the interior of the container and/or the interior of the conduit by the sensor. The flow of the fluid is regulated to the interior of the implant to regulate a volume of the implant based on the internal pressure and a medical condition of the person.

27 Claims, 5 Drawing Sheets

U.S. PATENT DOCUMENTS

| | | |
|---|---|---|
| 4,863,476 A | 9/1989 | Shepperd |
| 4,931,055 A | 6/1990 | Bumpus et al. |
| 4,932,975 A | 6/1990 | Main et al. |
| 4,969,887 A | 11/1990 | Sodhi |
| 4,969,888 A | 11/1990 | Scholten et al. |
| 5,011,484 A | 4/1991 | Breard |
| 5,047,055 A | 9/1991 | Bao et al. |
| 5,059,193 A | 10/1991 | Kuslich |
| 5,092,866 A | 3/1992 | Breard et al. |
| 5,098,433 A | 3/1992 | Freedland |
| 5,171,278 A | 12/1992 | Pisharodi |
| 5,171,280 A | 12/1992 | Baumgartner |
| 5,201,734 A | 4/1993 | Cozad et al. |
| 5,306,275 A | 4/1994 | Bryan |
| 5,306,310 A | 4/1994 | Siebels |
| 5,360,430 A | 11/1994 | Lin |
| 5,366,455 A | 11/1994 | Dove |
| 5,390,683 A | 2/1995 | Pisharodi |
| 5,395,370 A | 3/1995 | Muller et al. |
| 5,415,661 A | 5/1995 | Holmes |
| 5,437,672 A | 8/1995 | Alleyne |
| 5,454,812 A | 10/1995 | Lin |
| 5,458,641 A | 10/1995 | Ramirez Jimenez |
| 5,496,318 A | 3/1996 | Howland et al. |
| 5,518,498 A | 5/1996 | Lindenberg et al. |
| 5,545,229 A | 8/1996 | Parsons et al. ............... 623/17 |
| 5,549,679 A | 8/1996 | Kuslich |
| 5,554,191 A | 9/1996 | Lahille et al. |
| 5,562,736 A | 10/1996 | Ray et al. |
| 5,609,634 A | 3/1997 | Voydeville |
| 5,609,635 A | 3/1997 | Michelson |
| 5,628,756 A | 5/1997 | Barker, Jr. et al. |
| 5,645,597 A | 7/1997 | Krapiva |
| 5,645,599 A | 7/1997 | Samani |
| 5,665,122 A | 9/1997 | Kambin |
| 5,674,295 A | 10/1997 | Ray et al. |
| 5,676,702 A | 10/1997 | Ratron |
| 5,690,649 A | 11/1997 | Li |
| 5,702,452 A | 12/1997 | Argenson et al. |
| 5,702,455 A | 12/1997 | Saggar |
| 5,707,390 A | 1/1998 | Bonutti |
| 5,716,416 A | 2/1998 | Lin |
| 5,746,762 A | 5/1998 | Bass |
| 5,755,797 A | 5/1998 | Baumgartner |
| 5,810,815 A | 9/1998 | Morales |
| 5,836,948 A | 11/1998 | Zucherman et al. |
| 5,860,977 A | 1/1999 | Zucherman et al. |
| 5,976,186 A | 11/1999 | Bao et al. |
| 6,022,376 A | 2/2000 | Assell et al. |
| 6,048,342 A | 4/2000 | Zucherman et al. |
| 6,066,154 A | 5/2000 | Reiley et al. |
| 6,068,630 A | 5/2000 | Zucherman et al. |
| 6,126,689 A | 10/2000 | Brett |
| 6,127,597 A | 10/2000 | Beyar et al. |
| 6,132,464 A | 10/2000 | Martin |
| 6,187,048 B1 | 2/2001 | Milner et al. ............... 623/17.12 |
| 6,190,413 B1 | 2/2001 | Sutcliffe |
| 6,190,414 B1 | 2/2001 | Young |
| 6,214,050 B1 | 4/2001 | Huene |
| 6,293,949 B1 | 9/2001 | Justis et al. |
| 6,336,930 B1* | 1/2002 | Stalcup et al. ............... 606/284 |
| 6,348,053 B1 | 2/2002 | Cachia |
| 6,352,537 B1 | 3/2002 | Strnad |
| 6,364,883 B1 | 4/2002 | Santilli |
| 6,375,682 B1 | 4/2002 | Fleischmann et al. |
| 6,401,718 B1 | 6/2002 | Johnson et al. ............... 128/879 |
| 6,402,750 B1 | 6/2002 | Atkinson et al. |
| 6,402,751 B1 | 6/2002 | Hoeck et al. |
| 6,419,704 B1 | 7/2002 | Ferree |
| 6,425,923 B1 | 7/2002 | Stalcup et al. ............ 623/23.58 |
| 6,440,169 B1 | 8/2002 | Elberg et al. |
| 6,443,988 B2 | 9/2002 | Felt et al. ............... 623/17.12 |
| 6,451,019 B1 | 9/2002 | Zucherman et al. |
| 6,520,991 B2 | 2/2003 | Huene |
| 6,554,833 B2 | 4/2003 | Levy |
| 6,582,433 B2 | 6/2003 | Yun |
| 6,582,467 B1 | 6/2003 | Teitelbaum et al. |
| 6,592,585 B2 | 7/2003 | Lee et al. |
| 6,626,944 B1 | 9/2003 | Taylor |
| 6,645,207 B2 | 11/2003 | Dixon et al. |
| 6,685,742 B1 | 2/2004 | Jackson |
| 6,695,842 B2 | 2/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,533 B1 | 5/2004 | Lozier |
| 6,733,534 B2* | 5/2004 | Sherman ............... 623/17.16 |
| 6,736,818 B2 | 5/2004 | Perren et al. |
| 6,758,863 B2 | 7/2004 | Estes et al. |
| 6,761,720 B1 | 7/2004 | Senegas |
| 6,835,205 B2 | 12/2004 | Atkinson et al. |
| 6,905,512 B2 | 6/2005 | Paes et al. |
| 6,946,000 B2 | 9/2005 | Senegas et al. |
| 6,958,077 B2 | 10/2005 | Suddaby |
| 6,969,404 B2 | 11/2005 | Ferree |
| 6,981,975 B2 | 1/2006 | Michelson |
| 7,001,431 B2 | 2/2006 | Bao et al. ............... 623/17.12 |
| 7,011,685 B2 | 3/2006 | Arnin et al. |
| 7,041,136 B2 | 5/2006 | Goble et al. |
| 7,048,736 B2 | 5/2006 | Robinson et al. |
| 7,081,120 B2 | 7/2006 | Li et al. |
| 7,087,083 B2 | 8/2006 | Pasquet et al. |
| 7,097,648 B1 | 8/2006 | Globerman et al. |
| 7,163,558 B2 | 1/2007 | Senegas et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,377,942 B2 | 5/2008 | Berry |
| 7,442,208 B2 | 10/2008 | Mathieu et al. |
| 7,445,637 B2 | 11/2008 | Taylor |
| 7,582,106 B2 | 9/2009 | Teitelbaum et al. |
| 2001/0037117 A1 | 11/2001 | Gambale et al. ............... 606/108 |
| 2002/0143331 A1 | 10/2002 | Zucherman et al. |
| 2003/0153915 A1 | 8/2003 | Nekozuka et al. |
| 2003/0195628 A1 | 10/2003 | Bao et al. ............... 623/17.12 |
| 2004/0049202 A1 | 3/2004 | Berger ............... 606/90 |
| 2004/0082954 A1* | 4/2004 | Teitelbaum et al. ............ 606/61 |
| 2004/0083002 A1 | 4/2004 | Belef et al. |
| 2004/0097931 A1 | 5/2004 | Mitchell |
| 2004/0133204 A1 | 7/2004 | Davies |
| 2004/0167625 A1 | 8/2004 | Beyar et al. |
| 2004/0260397 A1 | 12/2004 | Lambrecht et al. |
| 2005/0010293 A1 | 1/2005 | Zucherman et al. |
| 2005/0049708 A1 | 3/2005 | Atkinson et al. |
| 2005/0165398 A1 | 7/2005 | Reiley |
| 2005/0187556 A1 | 8/2005 | Stack et al. ............... 606/79 |
| 2005/0203512 A1 | 9/2005 | Hawkins et al. |
| 2005/0203624 A1 | 9/2005 | Serhan et al. |
| 2005/0209601 A1* | 9/2005 | Bowman et al. ............... 606/90 |
| 2005/0209602 A1 | 9/2005 | Bowman et al. ............... 606/90 |
| 2005/0228391 A1 | 10/2005 | Levy et al. |
| 2005/0251259 A1 | 11/2005 | Suddaby ............... 623/17.12 |
| 2005/0261768 A1 | 11/2005 | Trieu |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0009779 A1 | 1/2006 | Collins et al. ............... 606/92 |
| 2006/0009851 A1 | 1/2006 | Collins et al. ............... 623/17.16 |
| 2006/0015181 A1 | 1/2006 | Elberg |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0136060 A1 | 6/2006 | Taylor |
| 2006/0184247 A1 | 8/2006 | Edidin et al. |

| | | |
|---|---|---|
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0235387 A1 | 10/2006 | Peterman |
| 2006/0235532 A1 | 10/2006 | Meunier et al. |
| 2006/0241613 A1 | 10/2006 | Bruneau et al. |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0293662 A1 | 12/2006 | Boyer, II et al. |
| 2006/0293663 A1 | 12/2006 | Walkenhorst et al. |
| 2007/0043362 A1* | 2/2007 | Malandain et al. ............ 606/61 |
| 2007/0142915 A1 | 6/2007 | Altarac et al. |
| 2007/0151116 A1 | 7/2007 | Malandain |
| 2007/0162000 A1 | 7/2007 | Perkins |
| 2007/0191838 A1 | 8/2007 | Bruneau et al. |
| 2007/0198091 A1 | 8/2007 | Boyer et al. |
| 2007/0225807 A1 | 9/2007 | Phan et al. |
| 2007/0233068 A1 | 10/2007 | Bruneau et al. |
| 2007/0233081 A1 | 10/2007 | Pasquet et al. |
| 2007/0233089 A1 | 10/2007 | DiPoto et al. |
| 2007/0270834 A1* | 11/2007 | Bruneau et al. ............... 606/61 |
| 2007/0276369 A1 | 11/2007 | Allard et al. |
| 2007/0276493 A1 | 11/2007 | Malandain et al. |
| 2007/0282443 A1 | 12/2007 | Globerman et al. |
| 2008/0021457 A1 | 1/2008 | Anderson et al. |
| 2008/0058934 A1 | 3/2008 | Malandain et al. |
| 2008/0161818 A1 | 7/2008 | Kloss et al. |
| 2008/0221685 A9 | 9/2008 | Altarac et al. |
| 2008/0262617 A1 | 10/2008 | Froehlich et al. |
| 2009/0270918 A1 | 10/2009 | Attia et al. |

FOREIGN PATENT DOCUMENTS

| | | |
|---|---|---|
| DE | 3922044 A1 | 2/1991 |
| DE | 4012622 C1 | 7/1991 |
| EP | 0322334 B1 | 2/1992 |
| EP | 0767636 B1 | 1/1999 |
| EP | 1004276 A1 | 5/2000 |
| EP | 1138268 A1 | 10/2001 |
| EP | 1302169 A1 | 4/2003 |
| EP | 1330987 A1 | 7/2003 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| SU | 988281 | 1/1983 |
| SU | 1484348 A1 | 6/1989 |
| WO | 94/26192 | 11/1994 |
| WO | 94/26195 | 11/1994 |
| WO | 98/20939 | 5/1998 |
| WO | 99/26562 | 6/1999 |
| WO | 99/59669 | 11/1999 |
| WO | 00/44319 | 8/2000 |
| WO | 01/54598 A1 | 8/2001 |
| WO | 03/057055 A1 | 7/2003 |
| WO | 2004/047689 A1 | 6/2004 |
| WO | 2004/047691 A1 | 6/2004 |
| WO | 2004/084768 A2 | 10/2004 |
| WO | 2005/002474 A1 | 1/2005 |
| WO | 2005/009300 A1 | 2/2005 |
| WO | 2005/011507 A1 | 2/2005 |
| WO | 2005/044118 A1 | 5/2005 |
| WO | 2005/048856 A1 | 6/2005 |
| WO | 2005/110258 A1 | 11/2005 |
| WO | 2006/064356 A1 | 6/2006 |
| WO | 2007/034516 A1 | 3/2007 |
| WO | 2007052975 A1 | 5/2007 |

OTHER PUBLICATIONS

"Tecnica Operatoria Per II Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Benzel et al., "Posterior Cervical Interspinous Compression Wiring and Fusion for Mid to Low Cervical Spinal Injuries," J. Neurosurg., Jun. 1989, ppp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," Spine, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Duff, "Methyl Methacrylate in Spinal Stabilization," Techniques in Spinal Fusion and Stabilization, Hitchon et al., eds., 1995, pp. 147-151, Ch. 14, Thieme, New York.

Ebara et al., "Inoperative Measurement of Lumbar Spinal Instability," Spine, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," Spine, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Posterieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," Spine, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 ° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," Spine, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," Spine, 2005, pp. 744-749, vol. 30, No. 7.

Scarfó, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," Spine, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopèdique, 1988, pp. 15-22.

Senegas et al., "Stabilisation Lombaire Souple," Instabilité Vertébrates Lombaires, Gastambide, ed., 1995, pp. 122-132, Expansion Scientifique Francaise, Paris, France.

Senegas, "La Ligamentoplastie Inter Vertébrate Lombaire, Alternative a L'Arthrodése," La Revue de Medécine Orthopédique, Jun. 1990, pp. 33-35, No. 20.

Senegas, "La Ligamentoplastie Intervertébrale, Alternative á L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-5169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumber Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrate, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation àun an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiese!, ed., Jun. 1994, pp. 116-123, vol. 6, No. 2.

Zucherman et al., "Clinical Efficacy of Spinal Instrumentation in Lumbar Degenerative Disc Disease," Spine, Jul. 1992, pp. 834-837, vol. 17, No. 7.

Kramer et al., "Intervetertebral Disk Diseases: Causes, Diagnosis, Treatment and Prophylaxis," pp. 244-249, Medical, 1990.

Zdeblick et al., "Two-Point Fixation of the Lumbar Spine Differential Stability in Rotation," Spine, 1991, pp. S298-S301, vol. 16, No. 6, Supplement.

* cited by examiner

SYSTEMS AND METHODS FOR ADJUSTING PROPERTIES OF A SPINAL IMPLANT

CROSS-REFERENCE TO RELATED APPLICATIONS

This application contains subject matter which is related to the subject matter of the following patent applications, each of which is assigned to the same assignee as this application and filed on the same day as this application. Each of the below listed applications is hereby incorporated herein by reference in its entirety:

"Surgical Spacer," by Kent Anderson, U.S. Ser. No. Unassigned, filed on the same day as the present application, application Ser. No. 11/438,940; and "Surgical Spacer with Shape Control," by Lange et al., U.S. Ser. No. Unassigned, filed on the same day as the present application, application Ser. No. 11/438,891.

TECHNICAL FIELD

The present invention relates generally to the field of surgery and medical implants, and more particularly, to surgical systems and methods for controlling the properties of a spinal implant.

BACKGROUND OF THE INVENTION

The human spine is a biomechanical structure with thirty-three vertebral members, and is responsible for protecting the spinal cord, nerve roots and internal organs of the thorax and abdomen. The spine also provides structure support for the body while permitting flexibility of motion. A significant portion of the population will experience back pain at some point in their lives resulting from a spinal condition. The pain may range from general discomfort to disabling pain that immobilizes the individual. Back pain may result from a trauma to the spine, be caused by the natural aging process, or may be the result of a degenerative disease or condition.

Procedures to remedy back problems sometimes require correcting the distance between vertebral members by inserting an intervertebral device (e.g., spacer) between the members. Dynamic interspinous spacers are currently used to treat patients with a variety of indications. Essentially, these patients present a need for distraction of the posterior elements (e.g., the spinal processes) of the spine using a mechanical device. Current clinical indications for such a device may include stenosis, disc herniation, facet arthropathy, degenerative disc disease and adjacent segment degeneration.

Currently, marketed interspinous devices include rigid and flexible spacers made from PEEK, titanium, silicone or some combination of other implantable materials. However, these devices require an open technique to be implanted, and many require destroying important anatomical stabilizers, such as the supraspinous ligament. Also, current devices are pre-formed and are not customizable for different sizes and dimensions of the anatomy of an interspinous area of an actual patient. Further, the stiffness or flexibility of the devices must be determined prior to the devices being inserted into the interspinous area.

Thus, a need exists for improved systems and methods for regulating the properties of a spinal implant based on the condition of a patient. The systems and methods disclosed herein address this need.

SUMMARY OF THE INVENTION

The shortcomings of the prior art are overcome and additional advantages are provided in one aspect through a method for controlling properties of a medical implant which includes locating the medical implant in an interspinous area between two spinal processes of a person. The medical implant is coupled to a container via a conduit. A fluid is received in a container interior of the container in fluid communication with the conduit. The fluid flows from the container toward the implant having an implant interior configured to receive the fluid. A pressure sensor is coupled to the interior of the container and/or a conduit interior of the conduit. An internal pressure is determined of the container interior and/or the conduit interior by the sensor. The flow of the fluid is regulated to the implant interior to regulate a volume of the implant based on the internal pressure and a medical condition of the person.

The present invention provides, in another aspect, a medical implant system which includes a container having an interior configured to receive a fluid. A conduit is in fluid communication with the container and a medical implant to allow fluid to flow from the container to an interior of the implant. A pressure sensor is coupled to a container interior of the container and/or a conduit interior of the conduit to allow a measurement of an internal pressure of the interior of the container and/or the interior of the conduit. A regulator is configured to regulate a flow of the fluid to the interior of the implant based upon the internal pressure.

The present invention provides, in a further aspect, a method for controlling properties of a medical implant which includes locating the spinal implant in an interspinous area between two spinal processes of a person. The medical implant is coupled to a container via a conduit and a fluid is received in a container interior of the container in fluid communication with the conduit. A first volume flows from the container to an implant interior of the implant with the implant interior having a nominal volume. The first volume is selected by determining a desired ratio of the first volume relative to the nominal volume based on the medical condition of the person.

The present invention provides, in yet another aspect, a system for controlling properties of a medical implant which includes a container having a container interior configured to receive a fluid. A conduit is in fluid communication with the container and an implant interior of the medical implant to allow fluid to flow from the container to the implant interior. The container also includes an indicator of a volume of the fluid therein. A regulator is configured to regulate a flow of the fluid to the implant interior.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter, which is regarded as the invention, is particularly pointed out and distinctly claimed in the claims at the conclusion of the specification. The foregoing and other objects, features, and advantages of the invention will be apparent from the following detailed description of preferred embodiments taken in conjunction with the accompanying drawings in which:

BEST MODE FOR CARRYING OUT THE INVENTION

In accordance with the principles of the present invention, a system and method for controlling properties of a spinal implant are provided.

Figure 1:
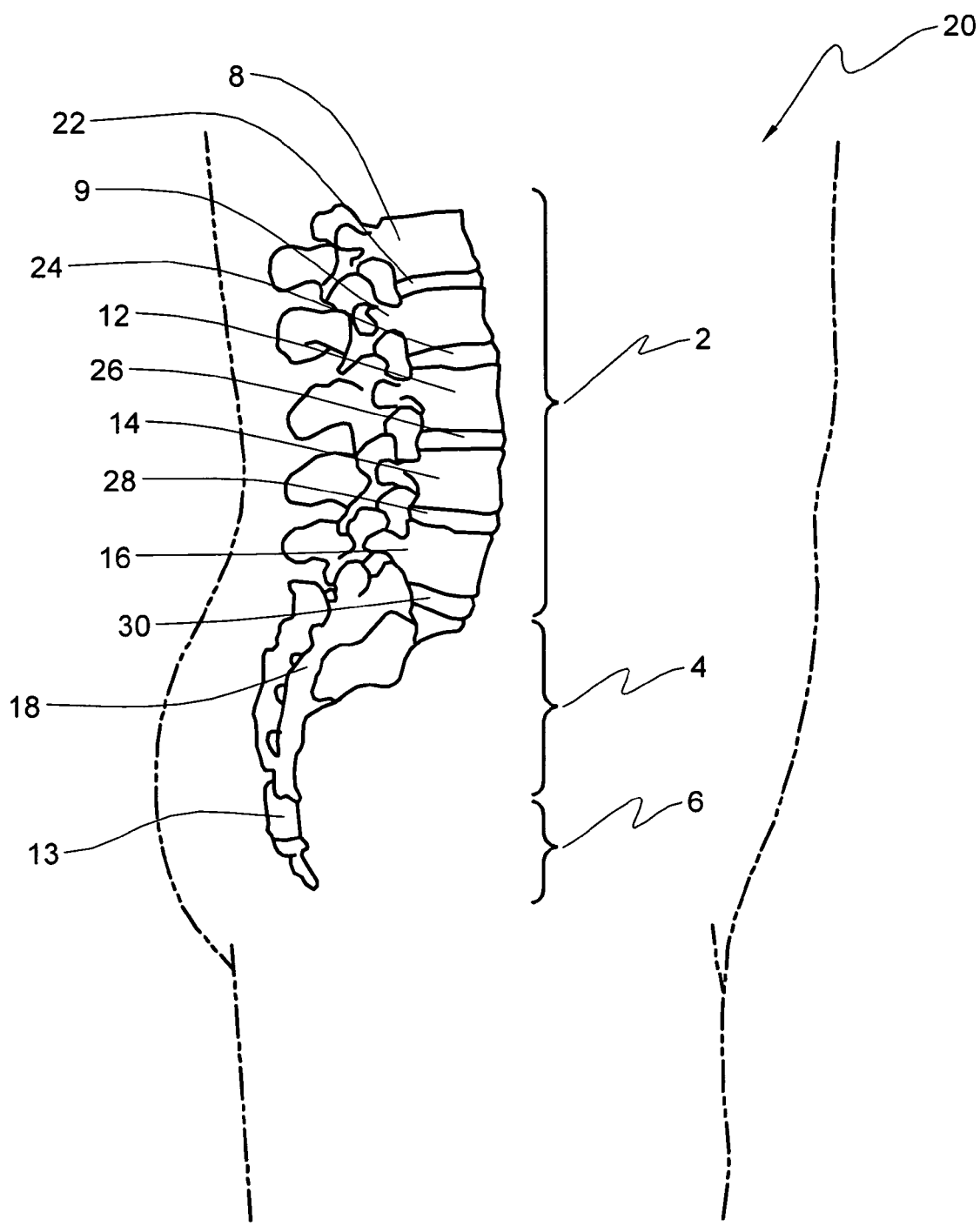
FIG. 1 is a side elevational view of a lower portion of a spine of a human in accordance with an aspect of the present invention.

Referring to FIG. 1, a portion of a spinal column 20 is shown. As depicted, spinal column 20 includes a lumbar region 2, a sacral region 4, and a coccygeal region 6. As is known in the art, column 20 also includes a cervical region and a thoracic region. For clarity and ease of discussion, the cervical region and the thoracic region are not illustrated. Lumbar region 2 includes a first lumbar vertebra 8, a second lumbar vertebra 9, a third lumbar vertebra 12, a fourth lumbar vertebra 14, and a fifth lumbar vertebra 16. Sacral region 4 includes a sacrum 18. Further, coccygeal region 6 includes a coccyx 13.

As depicted in FIG. 1, a first intervertebral lumbar disc 22 is disposed between first lumbar vertebra 8 and second lumbar vertebra 9. A second intervertebral lumbar disc 24 is disposed between second lumbar vertebra 9 and third lumbar vertebra 12. A third intervertebral lumbar disc 26 is disposed between third lumbar vertebra 12 and fourth lumbar vertebra 14. Further, a fourth intervertebral lumbar disc 28 is disposed between fourth lumbar vertebra 14 and fifth lumbar vertebra 16. Additionally, a fifth intervertebral lumbar disc 30 is disposed between fifth lumbar vertebra 16 and sacrum 18.

Figure 2:
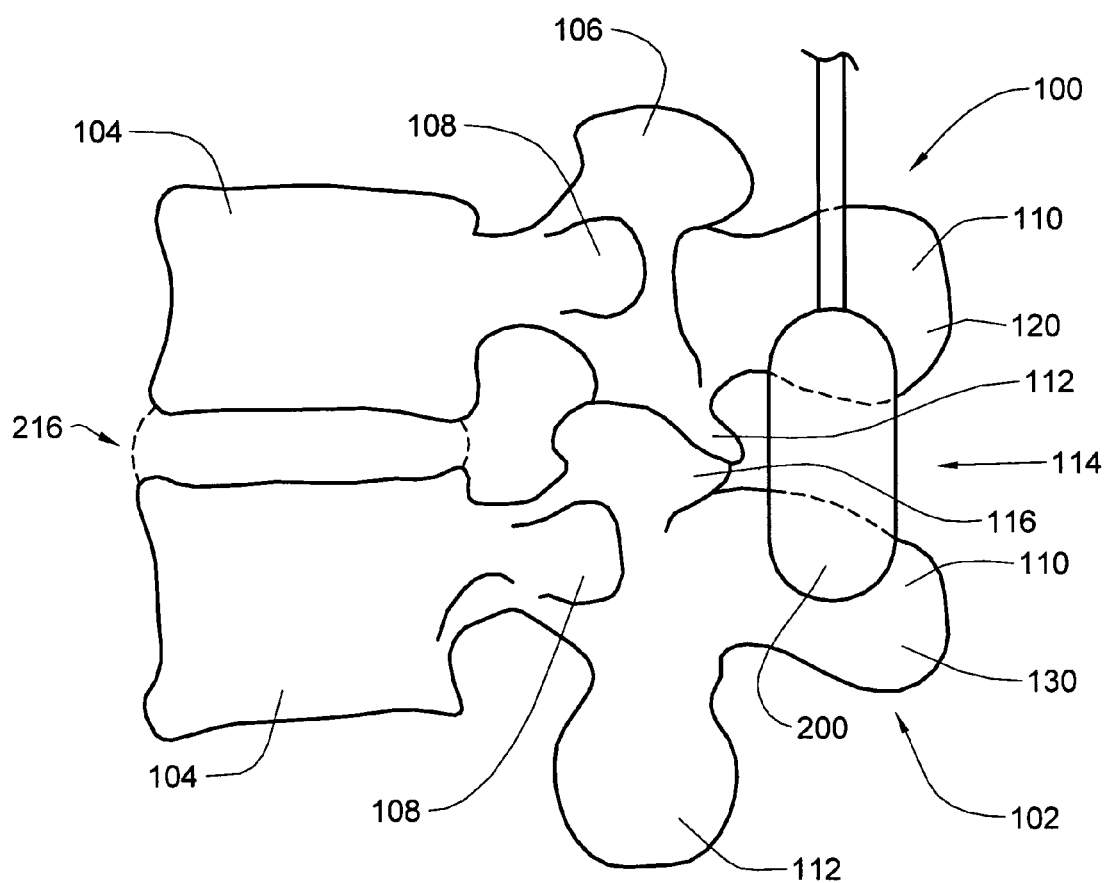
FIG. 2 is a side elevational view of two vertebrae of the spine of FIG. 1 having a spinal implant between spinal processes thereof in accordance with an aspect of the present invention.

FIG. 2 depicts a lateral view of two adjacent vertebrae, e.g., two of the lumbar vertebra 8, 9, 12, 14, 16 shown in FIG. 1. FIG. 2 illustrates a superior vertebra 100 and an inferior vertebra 102. As shown, each vertebra 100, 102 includes a vertebral body 104, a superior articular process 106, a transverse process 108, a spinous process 110 and an inferior articular process 112. FIG. 2 further depicts a space 114 that can be established between an upper spinous process 20 and a lower spinous process 130 by the removal of the interspinous ligament and any other boney or soft tissue needed for the insertion of a spinal implant 200.

Figure 3:
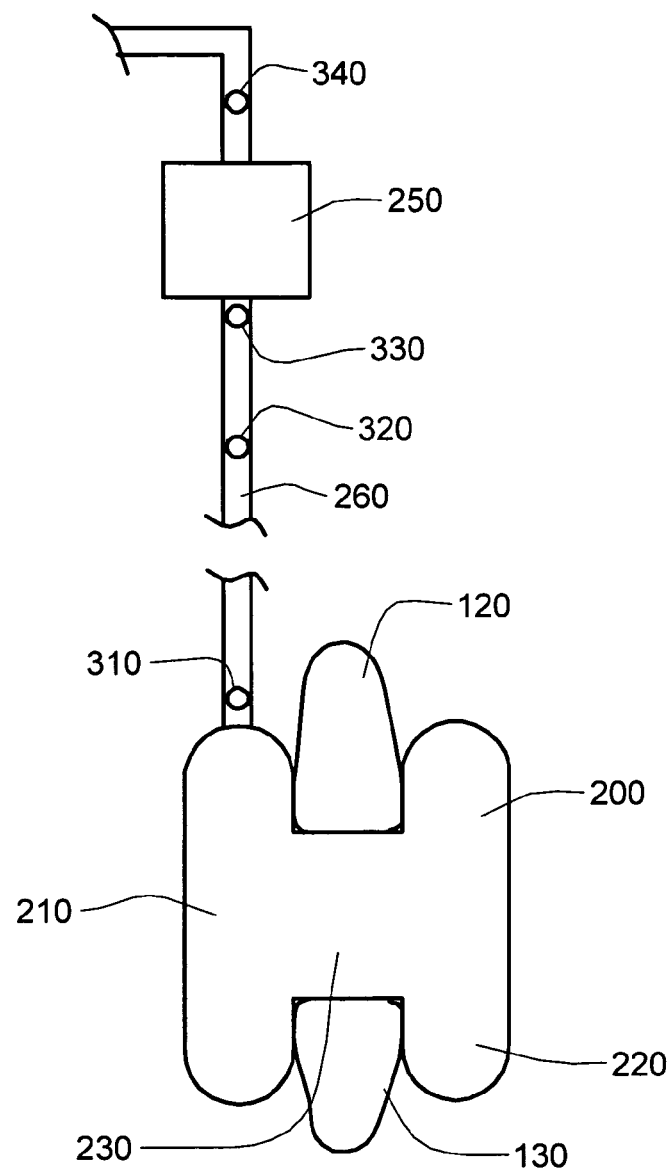
FIG. 3 is a front elevational view of the spinal implant and spinal processes of FIG. 2 with the implant being coupled to a conduit and a reservoir in accordance with an aspect of the present invention.

As depicted in FIG. 3, a spinal implant 200 may be H-shaped including two lateral portions 210 and 220 connected by a connecting portion 230. Lateral portions 210 and 220 are configured (e.g., shaped and dimensioned) to be received on opposite sides of upper spinal process 120 and lower spinal process 130. Connecting portion 230 is configured (e.g., shaped and dimensioned) to be received between upper spinal process 120 and lower spinal process 130 and to provide support and/or separation pressure therebetween. For example, connecting portion 230 may maintain a space between upper spinal process 120 and lower spinal process 130 in an area between the processes where an inter-spinal ligament has been removed.

Also, implant 200 may be compressed and inserted between the spinous processes (e.g., upper spinal process 120 and lower spinal process 130), and then inflated with a filling material such as a rapidly curing silicone or other biocompatible, curable material (e.g., a rapidly curing, tear-resistant elastomer). Implant 200 may be formed of impermeable materials, such as a polyester woven fabric, to inhibit leakage of such filling materials, but may be permeable to water and/or air. Further, the implant could include radio-opaque markers to facilitate the insertion of the implant via an X-ray image. Implant 200 may be coupled to a container 250 of a filling material, such as a biocompatible curable material, via a conduit 260. Further, the filling material could include barium sulfate or another radio-opaque marker to allow interoperative imaging of the filling material during and after implantation of the implant to determine placement, size, shape, or containment of the filling material, for example.

A system 300 for controlling properties of a spinal implant or spacer (e.g., implant 200) may include container 250, conduit 260 and one or more sensors to measure pressure and/or volume. For example, a first pressure sensor 310 may be located in conduit 260 adjacent to its connection with implant 200 as depicted in FIG. 3. A second pressure sensor 320 may be located along conduit 260 at a point between implant 200 and container 250. A third pressure sensor 330 may be located adjacent an exit point of the filling material from container 250 into conduit 260. A fourth pressure sensor 340 may be located in conduit 260 adjacent an entrance point of the filling material into container 250. The filling material may be forced into container 250 and/or forced from container 250 to implant 200 to inflate the implant to a desired level. Implant 200 may also include a detachable connection (not shown), which would allow the disconnection of conduct 260 relative to implant 200 after a desired amount of filling material (e.g., biocompatible curable material) has been received therein. Implant 200 and/or conduit 260 may also include a one-way valve as disclosed in co-owned U.S. Patent Application "Surgical Spacer," by Kent Anderson, U.S. Ser. No. Unassigned, filed on the same day as the present application, application Ser. No. 11/438,940; and "Surgical Spacer with Shape Control," by Lange et al., U.S. Ser. No. Unassigned, filed on the same day as the present application, application Ser. No. 11/438,891.

The inflation of implant 200 may fill space 114 such that upper spinous process 120 and lower spinous process 130 are separated or pushed away from one another. Also, implant 200 may minimize the movement of the spine in the area of space 114 between upper spinous process 120 and lower spinous process 130. Implant 200 may be inflated to a particular level depending on the desired freedom of movement or other factor desired for a patient receiving the implant. For example, implant 200 may be underfilled relative to a nominal theoretical volume thereof when it is desired for flexibility or a higher degree of freedom of movement to be provided while providing support of upper spinous process 120 relative to lower spinous process 130. Alternatively, when it is desired for the spine to be particularly stiff and a freedom of movement to be relatively low, implant 200 may be overfilled relative to a particular nominal or theoretical volume thereof. The overfilling of implant 200 may also result in the stretching thereof.

Further, in an underfilled state, upper spinous process 120 and lower spinous process 130 may be allowed to move toward one another while in an overfilled state, the spinous processes may be inhibited from moving toward one another. For example, implant 200 may have a nominal volume of 5 cubic centimeters and when a high degree of freedom of movement is desired, the implant may be filled to 4.5 cubic centimeters while when a more stiff situation, i.e., a lower degree of freedom of movement, is desired, the implant may be filled to 5.5 cubic centimeters. Also, the implant may be overfilled (e.g., greater than a nominal volume) in the case of a larger, heavier person or underfilled in the case of a smaller person.

In another example, implant 200 may be resistant to stretching and the interior thereof will not accept additional filling material beyond a particular volume. Further, implant 200 could be include a shell or jacket (not shown) which provides resistance to such stretching beyond a predetermined volume. Also, such jacket may itself have a degree of flexibility and/or resiliency to compliment that of the implant (e.g., implant 200) itself. For example, a combination of a semi-elastic jacket and an implant may be configured for use between 50%-150% of a nominal volume of the implant while a more rigid relatively inelastic jacket and implant may be utilized in a range of 90%-110% of a nominal volume of the implant. In a more specific example, a ratio of 1.05 to 1.00 of a filled implant relative to a nominal volume thereof may provide a very firm implant with more spacing between spinal processes and distraction thereof relative to an implant filled to the nominal volume. In a further example, an implant may be filled to a ratio of 0.95 to 1.00 relative a nominal volume to provide more flexibility and freedom of movement relative to an implant filled to such a nominal volume. Further, filling material for the implant may be chosen based on its stiffness, flexibility, and/or resiliency when cured. Moreover, implant 200 and/or a jacket enveloping and/or supporting implant 200 may be formed in any shape corresponding to various locations within the spinal column and particularly between spinal processes.

Also, the size, stiffness, strength or shape of an implant (e.g., implant 200) itself may be controlled the via the amount of material injected, flowed or otherwise delivered into the interior of the implant. Further, relative to an implant-patient system (e.g., the implant and adjacent spinal processes), the overall stiffness, range of motion, joint pressure and disorder correction, such as for scoliosis, spondy, and stenonis, may be controlled via the volume of material received by the implant. In addition to the volume of material injected into the interior of implant 200, the type or properties of the material may also affect the implant performance. For example, a material may be chosen based on the cure profile of a curable polymer or elastomer. Other examples of filling material include polyurethane, and hydrogels. It is preferable that such filling materials cure in situ after being injected into an implant, but such filling material could also be a non-curing viscous gel or other non-curing material.

As noted above, the filling material (e.g., a curable, biocompatible material) may be forced into container 250 and from there to conduit 260 and implant 200. The filling material may be forced into container 250 via a hand pump, an electric pump, or other means of forcing, delivering and/or regulating the filling material into a system (e.g., system 300) for supporting the spine of a person and particularly into reservoir 250, conduit 260, and to implant 200. In one unillustrated example, container 250 itself could be a pressurized syringe type delivery system and pressure may be applied thereto via a plunger portion (not shown) which forces the filling material toward an implant such as implant 200. In such an example, container 250 may include markings or indicia indicating the volume contained therein such that the volume and material sent or delivered toward implant 200 may be measured by a user merely by observing the amount of filling material remaining in container 250 relative to an original volume thereof. In a different example, the markings or indicia could indicate a percentage of filling material remaining within the container relative to the container when filled. The indicia could also indicate a ratio of a volume of an implant relative to a nominal volume as described above based on the volume of the filling material remaining or previously directed toward the implant. In another example, a volume or flow meter, or sensor, may serve the same function as the volume indicating markings, i.e., indicating a volume remaining in the container or received in an implant.

Also, the sensors described above (e.g., relative to pressure or flow) may be coupled to a controller (not shown) which may analyze the measurements of the sensors by comparing such measurements to pre-set criteria. For example, when a pressure measurement received by one of the sensors (e.g., sensor 310) reaches a pre-set criteria, a pump (not shown) or other means for forcing the filling material into reservoir 250 may terminate a pumping or injection force such that no further filling material is forced toward implant 200. The controller may electronically receive information from the sensors, electronically compare the information to the pre-set criteria and electronically cause the pump or other means for forcing material into reservoir 250 to stop forcing the material therein. Alternatively, one or more of the sensors (e.g., sensor 310, sensor 320, sensor 340) may be coupled to a display which may indicate the pressure at the particular location of each sensor. A user (e.g., a surgeon) may then manually terminate the pumping or forcing of the filling material toward the implant (e.g., implant 200). Also, the sensors described above could be replaced by, or used in conjunction with, other types of sensors such as for flow rate, temperature, or other parameters related to the injection of the filling material into the implant.

It will be understood by those skilled in the art that the above described controllers could be a portion of a computing unit (not shown) adapted to control, and receive information, from the sensors, or from various valves, regulators, switches and gauges utilized to control flowing fluid to the spinal implant (e.g., implant 200) such that the volume and/or pressurization of such an implant may be controlled. Such computing unit(s) (not shown) may be a processor or computing unit, for example, an IBM mainframe or server, a Hewlett Packard system running HP-UX, a Unix derivative Operating System, a personal computer, such as a personal computer with Microsoft WINDOWS as the operating system and based on the Intel PC architecture, or an Apple Macintosh System. The computing unit may include, for example, one or more central processing units, memory, one or more storage devices and one or more input/output devices, as is well known in the art. For example, the computing unit may have a display (not shown) to enable visual output for viewing by a user.

Figure 4:
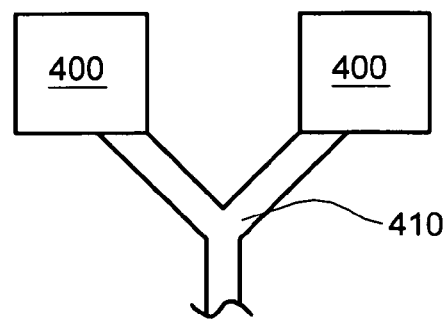
FIG. 4 is a block diagram of another embodiment of the present invention illustrating two reservoirs and a mixing chamber in accordance with an aspect of the present invention.

In another example depicted in FIG. 4, multiple containers 400 may be utilized to hold multiple components of a curable material prior to the mixing of the materials in a mixing chamber 410 and the injection, forcing or delivery of the materials into a conduit (e.g., conduit 260) and/or an implant (e.g., implant 200).

Figure 5:
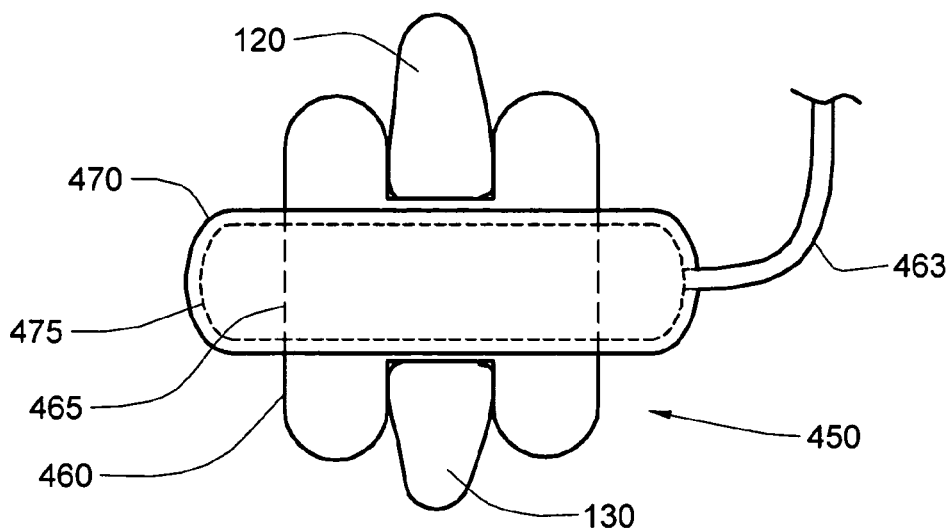
FIG. 5 is a front elevational view of another embodiment of a spinal implant between spinal processes thereof in accordance with an aspect of the present invention.
Figure 6:
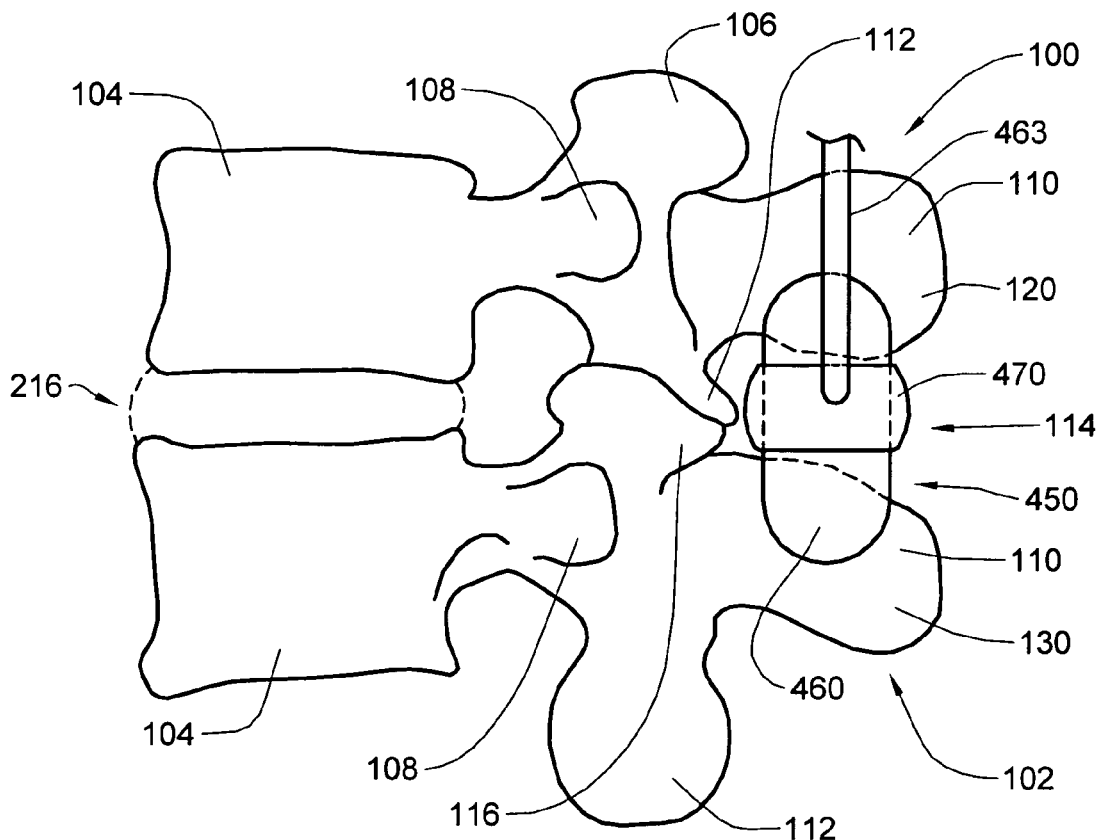
FIG. 6 is a side elevational view of the spinal implant of FIG. 5 in accordance with an aspect of the present invention.

In a further example depicted in FIGS. 5-6, an implant 450 may be received between upper spinal process 120 and lower spinal process 130, similar to the manner in which implant 200 is received therebetween, as depicted in FIG. 3. Implant 450 may include body portion 460 and a ring-shaped container 470 which encircles body portion 460. Container 470 may initially be empty when body portion 460 is inserted into space 114 between the spinal processes. Subsequent to the initial insertion of implant 450 into space 114, container 470 may be filled via a conduit 463 in a manner similar to that described for implant 200 above. For example, container 470 may be filled with the filling material described above to a particular volume to meet aging requirements of a patient at a particular period of time (e.g., months or years) after implant 450 is inserted between the spinal processes. Container 470 forms a cavity for receiving the filling material between an inner surface 475 of container 470 and an outer surface 465 of body portion 460.

Figure 7:
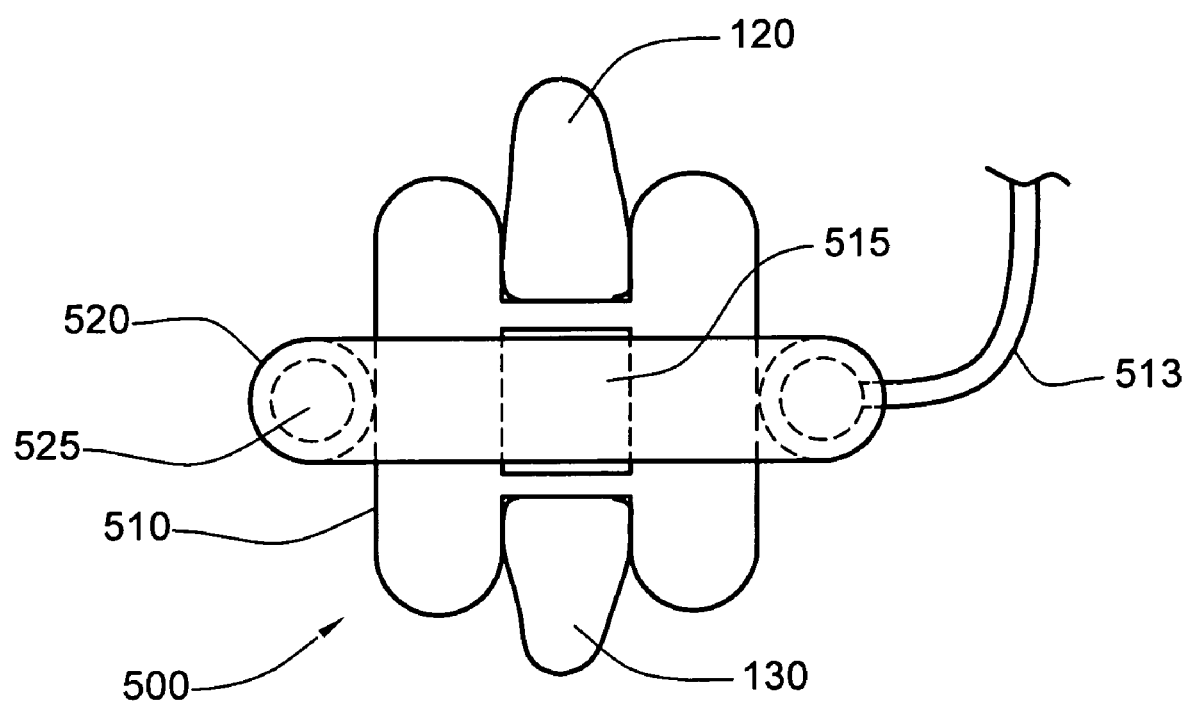
FIG. 7 is a front elevational view of another embodiment of a spinal implant between spinal processes thereof in accordance with an aspect of the present invention.

In yet a further example depicted in FIG. 7, implant 500 may be received between upper spinal process 120 and lower spinal process 130 similar to that described above for implant 450 and implant 200. Implant 500 may include a body portion 510 and a cylindrical-shaped container 520, which may receive filling material via a conduit 513 and the material may be held entirely within an interior 525 thereof, (i.e. the filling material does not directly contact body portion 510). Body portion 510 may also include a central cavity 515 which may allow body portion 510 additional flexibility and/or freedom of movement for a patient. For example, portions of body portion 510 opposite cavity 515 may move into the cavity to allow such further flexibility and/or freedom of movement. Further, both body portion 510 and body portion 460 (FIG. 4) may be fillable with a filling material in the same manner as implant 200, container 470 and container 520 described above.

In an unillustrated example, a body portion, such as body portion 460 or 510, could include a cavity (e.g., similar to central cavity 515) which receives a fillable container such as container 470 or container 520. Further, such a body portion and a container received therein may be fillable as described for implant 200, container 470 and container 520. It will be understood by one skilled in the art that the above described implants (e.g., implants 200, 450, and 500) and containers (e.g., containers 470 and 520) could be formed in any size and/or shape which allows them to be received between spinal processes, or within another portion of the spine, and to provide support to portions of the spine, such as the above described spinal processes.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

The invention claimed is:

1. A method for controlling properties of a medical implant, comprising:
locating the medical implant in an interspinous area between two spinal processes of a person, the medical implant including a first portion and a second portion, wherein the first portion and second portions each have an interior surface having first and second sections that face toward one another and an exterior surface having first and second sections that face away from one another, and wherein the interior surface of the second portion extends around the exterior surface of the first portion;
coupling the second portion to a container via a conduit;
flowing a fluid from an interior of the container to the second portion via the conduit such that the fluid is received in the second portion and outside of the first portion; wherein the first and second portions are fluidically isolated such that the fluid flowing to the second portion does not flow from the first portion into the second portion;
coupling a pressure sensor to at least one of the interior of the container and an interior of the conduit;
determining an internal pressure of at least one of the interior of the container and the interior of the conduit by the sensor;
regulating the flow of the fluid to the second portion to regulate a volume of the second portion based on the internal pressure and a medical condition of the person.

2. The method of claim 1 wherein the regulating the flow based on the internal pressure comprises regulating the flow to the second portion to control a freedom of movement of the two spinal processes relative to each other.

3. The method of claim 1 wherein the regulating the flow based on the internal pressure comprises regulating the flow to the second portion such that the second portion has a predetermined pressure, the pressure being based on the condition of the person.

4. The method of claim 1 wherein the first portion comprises two vertical side portions and a connecting portion, the connecting portion configured to be received between the spinal processes and the side portions configured to be received on at least a portion of lateral sides of the spinal processes.

5. The method of claim 1 wherein the sensor is located at an exit from the container, at a central portion of the conduit, or at an entrance to the implant.

6. The method of claim 1 further comprising providing an indication of the internal pressure to a user.

7. The method of claim 1 further comprising applying pressure to a manual pump to cause the flowing the fluid.

8. The method of claim 1 further comprising coupling a controller to the sensor and controlling the flowing the fluid by the controller based on the pressure.

9. The method of claim 1 further comprising measuring the flow of the fluid to obtain a flow measurement and controlling the volume flowing into the second portion based on the flow measurement.

10. The method of claim 1 wherein the container comprises a first container of a plurality of containers.

11. The method of claim 10 further comprising flowing fluid from the plurality of containers to a mixing chamber to mix the fluid from the plurality of containers prior to flowing the fluid to the conduit.

12. The method of claim 1 further comprising measuring a flow rate of the fluid toward the implant using a flow rate sensor.

13. The method of claim 1 wherein the fluid is received between the exterior surface of the first portion and the interior surface of the second portion.

14. The method of claim 1 wherein the fluid is received within an interior of the second portion such that the fluid does not contact the first portion.

15. The method of claim 1 wherein when fluid is received between the second portion and the first portion, the second portion inhibits bulging of the first portion.

16. The method of claim 1 wherein when fluid is received between the second portion and the first portion, the second portion controls the shape of the first portion.

17. The method of claim 1 further comprising:
providing a surgical access site to an interspinous area between two spinal processes of a person; and
closing the surgical access site while leaving the implant, including the first and second portions, in the interspinous area.

18. A method for controlling properties of a medical implant comprising:
locating the medical implant in an interspinous area between two spinal processes of a person, the medical implant including a first portion and a second portion disposed about the first portion, wherein the second portion has a filling nominal volume;
coupling the second portion to a container via a conduit;
flowing a first volume of a fluid from the container to the second portion via the conduit such that the fluid is received in the second portion and outside of the first portion;
selecting the first volume by determining a desired ratio of the first volume relative to the nominal volume based on a medical condition of the person.

19. The method of claim 18 wherein the flowing of the first volume of the fluid comprises flowing of the first volume of the fluid such that the first volume exceeds the nominal volume.

20. The method of claim 18 wherein the flowing of the first volume of the fluid comprises flowing the first volume of the fluid such that the first volume and the nominal volume have a ratio of about 1.05 to 1.00 relative to each other, respectively.

21. The method of claim 18 wherein the flowing of the first volume of the fluid comprises flowing the first volume of the fluid such that the first volume is less than the nominal volume.

22. In the method of claim 18 wherein the flowing of the first volume of the fluid comprises flowing the first volume of the fluid such that the first volume and the nominal volume have ratios of about 0.950 to 1.000 relative to each other, respectively.

23. The method of claim 18 wherein the flowing of the first volume of the fluid comprises flowing the fluid to the second portion to control a freedom of movement of the two spinal processes relative to each other.

24. The method of claim 18 wherein the first portion comprises two vertical side portions and a connecting portion, the connecting portion configured to be received between the spinal processes and the side portions configured to be received on at least a portion of lateral sides of the spinal processes.

25. The method of claim 24 further comprising flowing the fluid into the first portion such that the fluid flowing into the first portion does not flow from the first portion into the second portion.

26. The method of claim 25 further comprising regulating a vertical dimension of the connecting portion to regulate a distance between the spinal processes.

27. The method of claim 18 wherein the container comprises indicia indicating a volume of the fluid received in the container, and wherein the flowing the fluid comprises flowing the fluid based on observing the indicia.

* * * * *